(12) United States Patent
Wai-Chiu So et al.

(10) Patent No.: US 6,946,120 B2
(45) Date of Patent: *Sep. 20, 2005

(54) PHARMACEUTICAL COMPOSITION

(75) Inventors: Tony Wai-Chiu So, Doncaster East (AU); Peter Paul Deo, Oakleigh (AU); Russell John Tait, Deepdene (AU)

(73) Assignee: Connetics Australia Pty. Ltd., Victoria (AU)

(*) Notice: Subject to any disclaimer, the term of this patent is extended or adjusted under 35 U.S.C. 154(b) by 0 days.

This patent is subject to a terminal disclaimer.

(21) Appl. No.: 10/124,197

(22) Filed: Apr. 16, 2002

(65) Prior Publication Data

US 2002/0172649 A1 Nov. 21, 2002

Related U.S. Application Data

(63) Continuation of application No. 09/673,872, filed on Dec. 4, 2000.

(30) Foreign Application Priority Data

Apr. 22, 1998 (AU) .............................................. PP 3107

(51) Int. Cl.$^7$ .............................. A61K 7/06; A61K 6/00; A01N 25/06; A01N 25/02; A01N 47/40
(52) U.S. Cl. ........................ 424/70.1; 424/401; 424/40; 424/43; 514/880; 514/940; 514/946; 514/947
(58) Field of Search ................................ 424/400, 401, 424/70.1, 45, 47; 514/880, 945, 946, 947

(56) References Cited

U.S. PATENT DOCUMENTS

| | | |
|---|---|---|
| 4,139,619 A | 2/1979 | Chidsey, III |
| 4,596,812 A | 6/1986 | Chidsey, III et al. |
| 4,820,512 A | 4/1989 | Grollier |
| 4,828,837 A | 5/1989 | Quinn et al. |
| 4,866,067 A | 9/1989 | Di Schiena |
| 4,882,182 A | 11/1989 | Halls et al. |
| 4,888,354 A | 12/1989 | Chang et al. |
| 4,915,934 A | 4/1990 | Tomlinson |
| 4,938,953 A | 7/1990 | Pena et al. |
| 4,981,678 A | 1/1991 | Tomlinson |
| 5,006,332 A | 4/1991 | Grollier |
| 5,030,442 A | 7/1991 | Uster et al. |
| 5,041,439 A * | 8/1991 | Kasting et al. .......... 514/227.2 |
| 5,104,646 A | 4/1992 | Bolich, Jr. et al. |
| 5,156,836 A | 10/1992 | Uchikawa et al. |
| 5,183,817 A | 2/1993 | Bazzano |
| 5,225,189 A | 7/1993 | Pena |
| 5,516,504 A | 5/1996 | Tomlinson |
| 5,571,841 A | 11/1996 | Yu et al. |
| 5,578,599 A | 11/1996 | Diani et al. |
| 5,643,942 A | 7/1997 | Hester, Jr. et al. |
| 5,753,216 A * | 5/1998 | Leitch et al. ............ 424/70.12 |
| 5,783,202 A | 7/1998 | Tomlinson et al. |
| 5,788,155 A | 8/1998 | Martin et al. |
| 5,834,014 A | 11/1998 | Weiner et al. |
| 5,935,554 A | 8/1999 | Tomlinson |
| 6,211,250 B1 | 4/2001 | Tomlinson et al. |
| 6,231,875 B1 | 5/2001 | Sun et al. |
| 6,255,313 B1 | 7/2001 | Suzuki et al. |
| 6,267,949 B1 | 7/2001 | Halls |
| 6,284,234 B1 | 9/2001 | Niemiec et al. |
| 6,383,471 B1 | 5/2002 | Chen et al. |
| 6,419,913 B1 | 7/2002 | Niemiec et al. |
| 2003/0157046 A1 | 8/2003 | Imamura et al. |

FOREIGN PATENT DOCUMENTS

| | | |
|---|---|---|
| EP | 0 211 268 | 2/1987 |
| EP | 211268 A | 2/1987 |
| EP | 0 273 202 A2 | 7/1988 |
| EP | 0 331489 A2 | 9/1989 |
| EP | 0 160051 B1 | 1/1992 |
| EP | 0 599 819 A2 | 3/1994 |
| EP | 0 770 399 A2 | 5/1997 |
| EP | 1 070752 A2 | 1/2001 |
| JP | 62-036367 A | 2/1987 |
| JP | 63-045212 A | 2/1988 |

(Continued)

OTHER PUBLICATIONS

Ozawa and Nakajima, 1981, ["The need for low irritant hypoallergenic cosmetics, and problems for research and development,"] *Fragrance Journal* 48:43–46 (Japanese language, with full English translation).

R. Woodford and B.W. Barry, Bioavailability and Activity of Topical Corticosteroids from a Novel Drug Delivery System, the Aerosol Quick–Break Foam, Received from School of Pharmacy and Pharmacal Sciences, Purdue University, vol. 66, No. 1, Jan. 1977.

Albert Zorko Abram and Roderick Peter John Tomlinson, Mousses, Chapter 19, pp. 221–232, Soltec Research Pty Ltd., Rowville, Victoria, Australia, Jun. 2001.

Cowden, William, B. and Noel W. Jacobsen: "Pyrimidine N–oxides: The ionization constants of pyrimidine–2,4–diamine N–oxides;" *Aust. J. Chem.*; vol. 37, pp. 1195–1201 (1984).

Gorecki, D. et al., *Anal. Profiles Drug Sobst.*, vol. 17, pp. 185–219 (1988) esp. p. 190.

*Primary Examiner*—Gary Kunz
*Assistant Examiner*—Sharmila S. Gollamudi
(74) *Attorney, Agent, or Firm*—Townsend and Townsend and Crew LLP

(57) ABSTRACT

A pharmaceutical composition for topical administration, including, as the pharmaceutically active component, at least 5% by weight, based on the total weight of the composition of a piperidinopyrimidine derivative or a pharmaceutically acceptable salt thereof; an acid in an amount to completely solubilise the piperidinopyrimidine derivative or a pharmaceutically acceptable salt thereof; a solvent composition including at least two of water, a lower alcohol and a co-solvent selected from one or more of the group consisting of aromatic and polyhydric alcohols; wherein when the co-solvent includes propylene glycol, it is present in an amount of less than approximately 10% by weight.

21 Claims, No Drawings

FOREIGN PATENT DOCUMENTS

| | | |
|---|---|---|
| JP | 63-150211 A2 | 6/1988 |
| JP | 01-68309 A | 3/1989 |
| JP | 01-068308 A | 3/1989 |
| JP | 01-068310 A | 3/1989 |
| JP | 64-68308 A | 3/1989 |
| JP | 64-68309 A | 3/1989 |
| JP | 64-68310 A | 3/1989 |
| JP | 2-502822 | 6/1990 |
| JP | 9-5045387 B2 | 5/1995 |
| JP | 09071513 A | 3/1997 |
| JP | 09-188620 A | 7/1997 |
| JP | 9-188620 A | 7/1997 |
| JP | 9-188629 | 7/1997 |
| JP | 9-98447 | 10/1998 |
| JP | 2810040 B2 | 10/1998 |
| JP | 2810041 B2 | 10/1998 |
| JP | 10-265343 | 10/1998 |
| JP | 10-121876 | 11/1999 |
| JP | 10-158782 | 12/1999 |
| JP | 11-349451 * | 12/1999 |
| JP | 11349451 A | 12/1999 |
| WO | WO 8302558 | 8/1983 |
| WO | WO 85/01876 | 9/1985 |
| WO | WO 86/00196 | 1/1986 |
| WO | WO 88/01863 A1 | 3/1988 |
| WO | WO 88/07362 A | 3/1988 |
| WO | WO 8807362 | 10/1988 |
| WO | WO 89/07436 A1 | 8/1989 |
| WO | WO 92/04419 | 3/1992 |
| WO | WO 94/16732 | 8/1994 |
| WO | WO 95/25500 | 9/1995 |
| WO | WO 96/27376 | 9/1996 |
| WO | WO 97/03638 * | 2/1997 |
| WO | WO 97/12602 * | 4/1997 |
| WO | WO 98/00179 | 1/1998 |
| WO | WO 98/23291 | 6/1998 |
| WO | WO 88/04896 | 7/1998 |
| WO | WO 98/52525 | 11/1998 |
| WO | WO 99/20250 | 4/1999 |
| WO | WO 99/53923 | 10/1999 |
| WO | WO 00/15193 | 3/2000 |
| WO | WO 00/66172 | 11/2000 |
| WO | WO 01/76541 | 10/2001 |
| WO | WO 01/76605 | 10/2001 |

* cited by examiner

PHARMACEUTICAL COMPOSITION

The present application is a continuation and claims the benefit of earlier filed U.S. application Ser. No. 09/673,872, filed on Dec. 4, 2000, which is a National Phase application filed under 35 U.S.C. § 371 of PCT Application No.: PCT/AU99/00294, which PCT application claims priority to PP 3107 filed in the Australian Patent Office on Apr. 22, 1998 which is incorporated by reference in its entirety.

BACKGROUND OF THE INVENTION

The present invention relates to a vehicle system for a pharmaceutical composition comprising a piperidinopyrimidine derivative. More particularly minoxidil and to a pharmaceutical composition incorporating the vehicle system. Minoxidil is a pharmaceutically active ingredient having several indications including use as a hair growth stimulant.

Minoxidil has poor solubility in water and ethanol and pharmaceutical preparations currently marketed only contain a small percentage of minoxidil. That is, below 5%.

Numerous formulations comprising minoxidil have been published in the prior art including U.S. Pat. Nos. 4,139,619, 4,820,512, 5,104,646, 5,225,189, 4,938,953, 4,596,812, 5,006,332, 5,156,836 and 5,643,942. Many of the formulations require (or would require where the amount of minoxidil is greater than 5%) a very high percentage (often in the range of 30 to 50%) of propylene glycol or a similar glycol product in order to improve the solubility of minoxidil. Due to the viscosity and tack of propylene glycol, large amounts of propylene glycol or similar agents in a composition are not pharmaceutically or cosmetically elegant and may be unacceptable to the consumer. In addition, high concentrations of propylene glycol may cause local irritation and hypersensitivity upon application to the scalp.

It would accordingly be a significant advance in the art if a composition could be provided which would permit the inclusion of an increased percentage of the active ingredient, but without the disadvantages associated with a high propylene glycol concentration.

Accordingly, it is an object of the present invention to overcome, or at least alleviate, one or more of the difficulties and deficiencies related to the prior art. These and other objects and features of the present invention will be clear from the following disclosure.

SUMMARY OF THE INVENTION

Accordingly, the present invention in a first aspect provides a pharmaceutical composition for topical administration, including, as the pharmaceutically active component, at least 5% by weight, based on the total weight of the composition of a piperidinopyrimidine derivative or a pharmaceutically acceptable salt thereof;

an acid in an amount to substantially completely solubilise the piperidinopyrimidine derivative or a pharmaceutically acceptable salt thereof;

a solvent composition including a solvent selected from water and/or a lower alcohol and a co-solvent selected from one or more of the group consisting of aromatic and polyhydric alcohols; wherein when the co-solvent includes propylene glycol, it is present in an amount of less than approximately 10% by weight.

Applicants have surprisingly discovered that by adjusting the acid concentration of the composition the solubility of the piperidinopyrimidine derivatives may be significantly increased without the necessity of utilising large amounts of propylene glycol or optionally by excluding propylene glycol altogether. Accordingly the total amount of active in the composition may be significantly increased. In a preferred form, the pharmaceutically active component is present in amounts of approximately 5 to 25% by weight, preferably approximately 5 to 15% by weight, more preferably approximately 7.5 to 12% by weight.

Preferably the piperidinopyrimidine derivative is minoxidil. Preferably the minoxidil is present in the form of a salt. The salt may include acetate, citrate, succinate. benzoate, hydrochloride, sulphate, phosphate or lactate. Preferably an acetate or lactate salt of minoxidil is used. The acetate or lactate salts may exhibit enhanced solubility and improve the ability to incorporate increased amounts of the active component in the composition.

In a preferred form the acid is added in an amount sufficient to provide an apparent pH to the composition of approximately 7.0 or less. The apparent pH of the composition is preferably between approximately 5.0 to 7.0, more preferably between 6.0 to 6.5. Any suitable acid may be used to adjust the pH, including mineral acids, such as hydrochloric acid, sulphuric acid, nitric acid and phosphoric acid, or organic acids such as citric acid, acetic acid, succinic acid, or maleic acid, or mixtures thereof. Acetic acid or lactic acid is preferred.

In a preferred form the acid is present at a level that provides at least 0.01 Normal acid. Alternatively, the acid is present in an amount equal to, or greater than, the amount of the piperidinopyrimidine derivative in Normal amounts.

Preferably the lower alcohol is ethanol. The ratio of water to ethanol is preferably from approximately 9:1 to 1;9, more preferably approximately 1:1 to 1:3, by volume.

Preferably, the co-solvent includes benzyl alcohol. The benzyl alcohol may be present in amounts of approximately 2.5 to 95% by weight, preferably approximately 5 to 40% by weight, based on the total weight of the pharmaceutical composition.

Alternatively, or in addition the co-solvent may include a polyhydric alcohol, for example a polyol selected from the group consisting of 1,3-butylene glycol. propylene glycol, preferably polyethylene glycol 200 (PEG 200), polyethylene glycol 400 (PEG 400), hexylene glycol and dipropylene glycol, or glycerol. When propylene glycol is present, it may be present in amounts of approximately 10% by weight or less, preferably approximately 5% by weight, or less.

In compositions comprising 5% of minoxidil or greater, it is preferred to include benzyl alcohol in the composition. The benzyl alcohol may be present in amounts of up to 85% by weight, based on the total weight of the pharmaceutical composition.

In a preferred form the co-solvent system includes water and benzyl alcohol wherein the benzyl alcohol is in an amount of approximately 40 to 100% by weight, based on the total weight of the co-solvent system In a preferred form the water is present in an amount no greater than 60% by weight.

In a preferred aspect, the pharmaceutical composition includes approximately 5 to 12% by weight, based on the total weight of the composition, of a minoxidil or a minoxidil acid salt;

approximately 88 to 95% by weight of a solvent composition including approximately 10 to 70% by weight of ethanol, approximately 2.5 to 85% by weight of benzyl alcohol; and less than 10% by weight, propylene glycol.

The final presentation of the composition may be any suitable topical pharmaceutical preparation and may include solutions, lotions, ointments, mousses, foams, sprays, aerosols, shampoos and/or conditioners, gels, creams, pastes, and other preparations known in the art. The composition may also include other ingredients such as preservatives, buffers, stabilisers, propellants and the like.

Preferably the pharmaceutical composition is a mousse composition. The mousse composition may include a suitable propellant, for example hydrocarbons or chlorofluorocarbons. Alternatively the pharmaceutical composition may be a gel composition. The gel composition may include a suitable gelling agent, e.g. a cellulose derivative. A hydroxy propyl cellulose, for example that sold under the trade designation Klucel M, has been found to be suitable.

Where an aerosol formulation is used, the aerosol formulation may be a homogeneous, aqueous-alcoholic emulsion system. The aerosol formulation upon actuation produces a stabilized, homogeneous, expandable foam which breaks easily with shear. A composition of this type is sometimes referred to as a "mousse".

In a further preferred aspect, the pharmaceutical composition according to the present invention may further include an effective amount of a skin penetrating agent.

Suitable skin penetrating agents include alcohols such as dodecanol and oleyl alcohol; amines. such as isopropyl amine, diisopropyl amine, triethyl amine, triethanol amine, diisopropanolamine and ethylene diamine; carboxylic acids, such as oleic acid, linoleic acid and linolenic acid; esters, such as dibutyl sebacate, dibutyl phthalate, butyl benzoate and ethyl caprate; and others, such as Azone, N methyl pyrollidone, bile salts and urea.

All of the compositions herein may be actuated using propellants known per se in the pharmaceutical or cosmetic fields. Such propellants include hydrocarbons such as propane, isobutane or dimethyl ether and chlorofluorocarbons such as P-12, P114, and a 40:60 mixture thereof.

In the pharmaceutical composition according to the present invention, in addition to the above essential components, general purpose components ordinarily used in hair treatment compositions can be formulated, within a range which does not impair the effect of the present invention, including vitamins such as vitamin B.sub.6, vitamin E and derivatives thereof, and biotin; hair generating agents or hair generating aids such as panthothenic acid and derivatives thereof, glycylrrhetic acid and derivatives thereof, nicotinic acid esters such as benzyl nicotinate, cyclosporins, carpronium chloride, cepharanthine, oxendolone, diazoxide, minoxidil, and ethynylesteradiol; antibacterial agents such as hinokitiol, hexachlorophen, phenol, benzalkonium chloride, cetylpyridinium chloride, undecylenic acid, trichlorocarbanilide, and bithionol; refrigerants such as menthol; drugs such as salicylic acid, zinc and derivatives, thereof, and lactic acid and alkyl esters thereof; amino acids such as arginine; oil components such as olive oil, squalane, fluid paraffin, isopropyl myristate, higher fatty acids, and higher alcohols; perfumes; antioxidants; UV-ray absorbers; dyes-; humectants; thickeners; perfumes; colour additives and the like.

In a still further aspect of the present invention, there is provided a method for the treatment of hair loss and related indications in humans, which method includes providing a pharmaceutical composition for topical administration, including, as the pharmaceutically active component, at least 5% by weight, based on the total weight of the composition of a piperidinopyrimidine derivative or a pharmaceutically acceptable salt thereof;

an acid in an amount to substantially completely solubilise the piperidinopyrimidine derivative or a pharmaceutically acceptable salt thereof;

a solvent composition including a solvent selected from water and/or a lower alcohol and a co-solvent selected from one or more of the group consisting of aromatic and polyhydric alcohols; wherein when the co-solvent includes propylene glycol, it is present in an amount of less than approximately 10% by weight; and applying topically to the human scalp a therapeutically or prophylactically effective amount of the pharmaceutical composition.

The hair loss may be related to any of the forms of alopecia including male pattern alopecia. Related indications may include weakening of hair strength, loss of hair colour and the like.

Preferably the pharmaceutically active component includes a minoxidil or a minoxidil salt, more preferably a minoxidil acetate, succinate or citrate salt.

More preferably the pharmaceutical composition includes approximately 5 to 12% by weight, based on the total weight of the composition, of a minoxidil or a minoxidil acid salt;

approximately 88 to 95% by weight of a solvent composition including approximately 10 to 70% by weight of ethanol.

approximately 2.5 to 85% by weight of benzyl alcohol; and less than 10% by weight, propylene glycol.

The present invention will now be more fully described with reference to the accompanying figures and examples. It should be understood, however, that the description following is illustrative only and should not be taken in any way as a restriction on the generality of the invention described above.

In each of the following examples it was necessary to add an appropriate amount of acid to ensure equivalent acid normality. The standard technique for such an adjustment is to measure the apparent pH of the solution.

In the examples, the apparent pH of each formulation was measured once prepared. The measured taken as the apparent pH due to the high proportion of organic modifiers in the formulations. Typically, 0.5% (w/w) glacial acetic acid (0.1M) would be used in the formulation, which would equate to a pH of 1.0 in an aqueous system when no other components are contributing to the pH of the solution.

EXAMPLE 1

Topical Minoxidil Lotion 5% with no Propylene Glycol

| | |
|---|---|
| Minoxidil | 5.00% |
| Ethanol | 60.3% |
| Polysorbate 60 | 0.4% |
| Polyoxyethylene lauryl alcohol | 1.00% |
| Acetic Acid | 0.6 |
| Purified Water | to total 100% |

The apparent pH of the final formulated solution was measured at 6.24.

EXAMPLE 2

Topical Minoxidil Mousse 5% for Hair Treatment

| | |
|---|---|
| Minoxidil | 5.00% |
| Cetyl Alcohol | 2.20% |
| Stearyl Alcohol | 1.00% |
| Ethanol | 51.8 |
| Polysorbate 60 | 0.4% |
| Polyoxyethylene lauryl alcohol | 1.00% |
| Propylene Glycol | 5.00% |
| Propellant P75 | 4.30% |
| Acetic Acid | qs. pH 6.0 |
| Purified water | to total 100% |

EXAMPLE 3

Topical Minoxidil Lotion 8% for Hair Treatment

| | |
|---|---|
| Minoxidil | 8.00% |
| Ethanol | 50.50% |
| Polysorbate 60 | 0.4% |
| Polyoxyethylene lauryl alcohol | 1.00% |
| Nitric Acid | qs. pH 6.0 |
| Propylene Glycol | 7.30% |
| Benzyl Alcohol | 5.00% |
| Purified Water | to total 100% |

EXAMPLE 4

Topical 8% (w/w) Minoxidil Solution

| | |
|---|---|
| Minoxidil | 8.0% |
| Ethanol | 50.5% |
| Crilet 3 | 0.4% |
| Teric 12A4 | 1.0% |
| Glacial Acetic Acid | 0.3% |
| Propylene Glycol | 7.5% |
| Benzyl Alcohol | 5.0% |
| Purified Water | to total 100% |

The apparent pH of the final formulated solution was measured at 6.24.

EXAMPLE 5

Topical Minoxidil Lotion 10% for Hair Treatment

| | |
|---|---|
| Minoxidil | 10.00% |
| Ethanol | 48.0% |
| Polysorbate 60 | 0.4% |
| Polyoxyethylene lauryl alcohol | 1.00% |
| Acetic Acid | qs. pH 6.0 |
| Propylene Glycol | 10.0% |
| Benzyl Alcohol | 5.00% |
| Purified Water | to total 100% |

EXAMPLE 6

Topical Minoxidil Lotion 10% for Hair Treatment

| | |
|---|---|
| Minoxidil | 10.00% |
| Ethanol | 47.50% |
| Polysorbate 60 | 0.4% |
| Polyoxyethylene lauryl alcohol | 1.00% |
| Acetic Acid | qs. pH 6.0 |
| Benzyl Alcohol | 15.00% |
| Purified Water | to total 100% |

EXAMPLE 7

Topical 10% (w/w) Minoxidil Solution

| | Formulation 3a | Formulation 3b |
|---|---|---|
| Minoxidil | 10.00% | 10.00% |
| Ethanol | 46.80% | 44.20% |
| Crillet 3 | 0.4% | 0.4% |
| Teric 12A4 | 1.0% | 1.0% |
| Glacial Acetic Acid | 1.0% | 0.3% |
| Propylene Glycol | 10.0% | nil |
| Benzyl Alcohol | 5.00% | 2.00% |
| Purified Water | to total 100% | to total 100% |

The apparent pH of the final formulated solutions was measured at 6.0 and 6.5 for formulations 3a and 3b, respectively.

EXAMPLE 8

Topical Minoxidil Lotion 11% for Hair Treatment

| | |
|---|---|
| Minoxidil | 11.00% |
| Ethanol | 44.20% |
| Polysorbate 60 | 0.4% |
| Polyoxyethylene lauryl alcohol | 1.00% |
| Acetic Acid | qs. pH 6.0 |
| Benzyl Alcohol | 20.00% |
| Purified Water | to total 100% |

EXAMPLE 9

Topical Minoxidil Lotion 12% for Hair Treatment

| | |
|---|---|
| Minoxidil | 12.00% |
| Ethanol | 42.7% |
| Polysorbate 60 | 0.4% |
| Polyoxyethylene lauryl alcohol | 1.00% |
| Acetic Acid | qs. pH 6.0 |
| Benzyl Alcohol | 20.00% |
| Purified Water | to total 100% |

EXAMPLE 10

Topical Minoxidil Lotion 12% for Hair Treatment

| | |
|---|---|
| Minoxidil | 12.00% |
| Ethanol | 42.7% |
| Polysorbate 60 | 0.4% |
| Polyoxyethylene lauryl alcohol | 1.00% |
| Acetic Acid | qs. pH 6.0 |
| Benzyl Alcohol | 10.00% |
| Propylene Glycol | 10.00% |
| Purified Water | to total 100% |

EXAMPLE 11

Topical Minoxidil Lotion 12% for Hair Treatment

| | |
|---|---|
| Minoxidil | 12.00% |
| Ethanol | 42.7% |
| Polysorbate 60 | 0.4% |
| Polyoxyethylene lauryl alcohol | 1.00% |
| Acetic Acid | qs. pH 6.0 |
| Benzyl Alcohol | 15.00% |
| Propylene Glycol | 5.00% |
| Purified Water | to total 100% |

There appear to be no obvious gross stability issues associated with any of the formulations. The levels of minoxidil were assayed in formulations 1 and 3a after they had been stored for one and three months at 4° C. and 50° C. No measurable loss in potency was observed.

An aqueous gel was prepared by adding 0.75% (w/w) Klucel M (hydroxypropyl cellulose) to Example 4. The viscosity of the gel was measured at 2400 cPoise at 20° C.

EXAMPLE 12

Investigations were carried out to determine which of the components present in Example 7 (10% (w/w) minoxidil solution) were contributing to the solubilisation of minoxidil. The investigation was split into three sections:

Effect of Co-solvent

Effect of pH

Effect of Salt

The solubility determination involved preparation of saturated solutions of minoxidil in the media of interest. These solutions were then filtered (0.45 µm) and analysed against a standard curve by means of direct UV spectroscopy.

Aqueous Unbuffered Solubility of Minoxidil

The aqueous solubility of minoxidil was found to be 2.2 mg/mL.

Effect of Co-Solvent

The solubility of minoxidil was determined in each of the co-solvents, benzyl alcohol, glycerol, propylene glycol and ethanol. Additionally, the solubility of minoxidil was determined in 10% (w/w) solutions of each of the co-solvents, ethanol, propylene glycol and glycerol in water. A 4% (w/w) solution of benzyl alcohol was used since this was found to be the limit of the solubility of benzyl alcohol in water. The following table summarises the results of these studies.

| Sample | Minoxidil Solubility (mg/mL) |
|---|---|
| Benzyl alcohol | 125.1 |
| Glycerol | 47.3 |
| Propylene Glycol | 86.9 |
| Ethanol | 18.8 |
| 10% (w/w) Ethanol/Water | 3.4 |
| 10% (w/w) Propylene Glycol/Water | 3.0 |
| 4% (w/w) Benzyl Alcohol/Water | 4.5 |
| 10% (w/w) Glycerol/Water | 2.7 |

Analysis indicated that of the systems studied only the use of pure benzyl alcohol would result in the desired 10% (w/w) minoxidil solution.

Effect of Apparent pH

Attempts were made to prepare saturated solutions of minoxidil in acetate buffers at apparent pH's 2.5, 3.5, 4.6, 5.0 and 6.0. Saturated solutions were achieved with those pHs above the pKa of minoxidil (4.61), the results of which are summarised in the following table.

| pH | Minoxidil Solubility (mg/mL) |
|---|---|
| 6.0 | 2.5 |
| 5.0 | 4.1 |
| 4.6 | 11.3 |

It was not possible to determine the solubility limits of minoxidil at pH's below it's pKa, as minoxidil was found to be extremely soluble in acidic media and the buffer used had insufficient capacity to avoid the drift in pH observed with additions of minoxidil to the solution. The maximum minoxidil concentration studied was 22 mg/mL and was found to be completely soluble in pH 2.5 and 3.5 solutions at this concentration. The following table outlines the maximum solubility that would be expected in an acidic aqueous media knowing the solubility of the base form of minoxidil is 2.2 mg/mL and assuming infinite solubility of the acid form of minoxidil.

| pH | Minoxidil Solubility (mg/mL) |
|---|---|
| 3.6 | 22.0 |
| 3.0 | 87.6 |
| 2.6 | 220.0 |
| 2.0 | 876.0 |

Effect of Salt

Minoxidil base was used for these studies with the appropriate salt (acetate or HCl) formed in situ. As discussed above the use of low pH acetate buffers significantly increased the solubility of minoxidil.

The major factors affecting the solubilisation of minoxidil in an aqueous environment were found to be:

The type and proportion of co-solvents present in the formulation

The pH of the final formulated solution

The amount of minoxidil used

The acid form of minoxidil has been shown to be much more soluble in an aqueous environment. The use of co-solvents has been shown to enhance the solubility of the minoxidil free base. The co-solvents may also enhance the solubility of the acid form. The use of an appropriate salt enhances the solubility of the acid form of minoxidil.

Therefore, a combination of these three factors may be used to optimise the solubility of minoxidil in a topical solution based formulation.

All the above examples were stored at room temperature and no crystallisation or precipitation was observed for at least 10 days.

Please note all percentages are based upon the total weight of the composition unless otherwise specified.

It will be understood that the invention disclosed and defined in this specification extends to all alternative combinations of two or more of the individual features mentioned or evident from the text or drawings. All of these different combinations constitute various alternative aspects of the invention.

It will also be understood that the term "comprises" (or its grammatical variants) as used in this specification is equivalent to the term "includes" and should not be taken as excluding the presence of other elements or features.

What is claimed is:

1. A homogeneous aerosol formulation, said homogeneous aerosol formulation consisting essentially of:
   approximately 5% or greater by weight of minoxidil or a pharmaceutically acceptable salt thereof;
   an acid in an amount effective to solubilize the minoxidil or a pharmaceutically acceptable salt thereof, wherein the acid is a mineral acid selected from the group consisting of hydrochloric acid, sulphuric acid, nitric acid, and phosphoric acid, or an organic acid selected from the group consisting of citric acid, acetic acid, succinic acid, maleic acid, benzoic acid, lactic acid and mixtures thereof; a solvent of water and a lower alcohol wherein the ratio of water to alcohol is in a range of approximately 9:1 to 1:9 by volume; and a co-solvent of a polyhydric alcohol selected from 1,3-butylene glycol, polyethylene glycol, hexylene glycol, dipropylene glycol, glycerol or propylene glycol at less than approximately 10% by weight;
   wherein the final product of the homogeneous aerosol formulation is foam or a mousse.

2. A homogeneous aerosol formulation according to claim 1, wherein the acid is added in an amount sufficient to provide an apparent pH to the composition of approximately 7.0 or less.

3. A homogeneous aerosol formulation according to claim 1, wherein the minoxidil or pharmaceutically acceptable salt thereof is present in an amount of from approximately 5 to 25% by weight.

4. A homogeneous aerosol formulation according to claim 3, wherein the minoxidil or pharmaceutically acceptable salt thereof is present in an amount of approximately 7.5 to 12% by weight.

5. A homogeneous aerosol formulation according to claim 2, wherein the acid provides to the composition an apparent pH in the range of approximately 5.0 to 7.0.

6. A homogeneous aerosol formulation according to claim 5, wherein the acid is acetic acid or lactic acid.

7. A homogeneous aerosol formulation according to claim 1 wherein the lower alcohol is ethanol.

8. A homogeneous aerosol formulation according to claim 7, wherein the ratio of water to ethanol is in a range of approximately 1:1 to 1:3 by volume.

9. A homogeneous aerosol formulation according to claim 1 wherein the co-solvent is selected from glycerol, 1,3-butylene glycol or propylene glycol.

10. A homogeneous aerosol formulation according to claim 1, wherein the acid is present at a level that provides at least 0.01 Normal acid.

11. A homogeneous aerosol formulation according to claim 1, wherein the acid is present in an molar amount equal to or greater than the amount of the minoxidil or a pharmaceutically acceptable salt thereof in Normal amounts.

12. A homogeneous aerosol formulation according to claim 1, wherein the minoxidil or pharmaceutically acceptable salt thereof is minoxidil acetate or minoxidil lactate.

13. A homogeneous aerosol formulation according to claim 1, including
   approximately 5 to 12% by weight, based on the total weight of the composition, of minoxidil or pharmaceutically acceptable salt thereof;
   approximately 24 to 33% by weight water;
   approximately 43 to 60% by weight of ethanol; and
   less than 10% by weight, propylene glycol.

14. A homogeneous aerosol formulation, said homogeneous aerosol formulation consisting essentially of:
   approximately 5% by weight of minoxidil or a pharmaceutically acceptable salt thereof;
   an acid in an amount effective to solubilise the minoxidil or pharmaceutically acceptable salt thereof, wherein the acid is a mineral acid selected from the group consisting of hydrochloric acid, sulphuric acid, nitric acid, and phosphoric acid, or an organic acid selected from the group consisting of citric acid, acetic acid, succinic acid, maleic acid, benzoic acid, lactic acid and mixtures thereof; and
   water, ethanol, and less than approximately 10% by weight of propylene glycol;
   wherein the ratio of water to alcohol is in a range of approximately 9:1 to 1:9 by volume; wherein the final product of the homogeneous aerosol formulation is a foam or a mousse.

15. A homogeneous aerosol formulation according to claim 14, wherein the propylene glycol is approximately 5% or less by weight.

16. A homogeneous aerosol formulation according to claim 14, further comprising approximately 24 to 33% by weight water and approximately 43 to 60% by weight of ethanol.

17. A homogeneous aerosol formulation according to claim 14, wherein the acid is lactic acid.

18. A homogeneous aerosol formulation, said homogeneous aerosol formulation consisting essentially of:
   approximately 5% by weight of minoxidil or a pharmaceutically acceptable salt thereof;
   an acid in an amount effective to solubilise the minoxidil or pharmaceutically acceptable salt thereof, wherein the acid is a mineral acid selected from the group consisting of hydrochloric acid, sulphuric acid, nitric acid, and phosphoric acid, or an organic acid selected from the group consisting of citric acid, acetic acid, succinic acid, maleic acid, benzoic acid, lactic acid and mixtures thereof;
   water and ethanol, wherein the ratio of water to alcohol is in a range of approximately 9:1 to 1:9 by volume;
   cetyl alcohol, stearyl alcohol and polysorbate 60; and
   approximately 5% or less by weight of propylene glycol;
   wherein the final product of the homogeneous aerosol formulation is a foam or a mousse.

19. A method for the treatment of hair loss and related indications in humans comprising the step of applying topically to the human scalp a therapeutically or prophylactically effective amount of a homogeneous aerosol formulation wherein the final product is a foam or a mousse that breaks with shear according to any one of claims 1–4, 5, 6, 7, or 8–18.

20. A formulation comprising a homogeneous aerosol formulation according to any one of claims 1–4, 5, 6, 7, or 8–18 and a suitable propellant.

21. A homogeneous aerosol formulation, said aerosol formulation consisting essentially of:
- approximately 5% by weight of minoxidil or a pharmaceutically acceptable salt thereof;
- an acid in an amount effective to solubilise the minoxidil or pharmaceutically acceptable salt thereof, wherein the acid is a mineral acid selected from the group consisting of hydrochloric acid, sulphuric acid, nitric acid, and phosphoric acid, or an organic acid selected from the group consisting of citric acid, acetic acid, succinic acid, maleic acid, benzoic acid, lactic acid and mixtures thereof;
- water and ethanol, wherein the ratio of water to alcohol is in a range of approximately 9:1 to 1:9 by volume;
- cetyl alcohol, stearyl alcohol and polysorbate 60;
- approximately 5% or less by weight of propylene glycol; and
- an antioxidant,
- wherein the final product of the homogeneous aerosol formulation is a foam or a mousse.

* * * * *

UNITED STATES PATENT AND TRADEMARK OFFICE
CERTIFICATE OF CORRECTION

PATENT NO. : 6,946,120 B2 Page 1 of 1
DATED : April 16, 2002
INVENTOR(S) : Wai-Chiu So et al.

It is certified that error appears in the above-identified patent and that said Letters Patent is hereby corrected as shown below:

Column 10,
Line 3, insert -- molar -- before "amount".

Signed and Sealed this

Twenty-first Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,946,120 B2 Page 1 of 1
DATED : September 20, 2005
INVENTOR(S) : Wai-Chiu So et al.

It is certified that error appears in the above-identified patent and that said Letters Patent is hereby corrected as shown below:

Column 10,
Line 3, insert -- molar -- before "amount".

This certificate supersedes Certificate of Correction issued March 21, 2006.

Signed and Sealed this

Twenty-fifth Day of April, 2006

JON W. DUDAS
*Director of the United States Patent and Trademark Office*